US012576077B2

(12) United States Patent
Park et al.

(10) Patent No.: US 12,576,077 B2
(45) Date of Patent: Mar. 17, 2026

(54) COMPOSITION FOR PREVENTING, ALLEVIATING OR TREATING CANCER

(71) Applicant: CKP Therapeutics, Inc., Lowell, MA (US)

(72) Inventors: Ki Cheong Park, Lowell, MA (US); Seokmo Kim, Lowell, MA (US)

(73) Assignee: CKP THERAPEUTICS, INC., Lowell, MA (US)

( * ) Notice: Subject to any disclaimer, the term of this patent is extended or adjusted under 35 U.S.C. 154(b) by 409 days.

(21) Appl. No.: 18/238,961

(22) Filed: Aug. 28, 2023

(65) Prior Publication Data

US 2023/0404997 A1 Dec. 21, 2023

Related U.S. Application Data

(62) Division of application No. 17/409,233, filed on Aug. 23, 2021, now Pat. No. 11,738,021.

(51) Int. Cl.

*A61K 31/4745* (2006.01)
*A61K 31/282* (2006.01)
(Continued)

(52) U.S. Cl.

CPC ........ *A61K 31/4745* (2013.01); *A61K 31/282* (2013.01); *A61K 31/337* (2013.01);
(Continued)

(58) Field of Classification Search

CPC .............. A61K 2300/00; A61K 31/282; A61K 31/337; A61K 31/44; A61K 31/4745;
(Continued)

(56) References Cited

U.S. PATENT DOCUMENTS 5,914,402 A * 6/1999 Choi .................... C07D 471/04 546/89
7,973,163 B2 7/2011 Kajino et al. ................... 546/80
(Continued)

FOREIGN PATENT DOCUMENTS

| | | | |
|---|---|---|---|
| WO | 2017085053 | 5/2017 | C07D 471/04 |
| WO | 2018146390 | 8/2018 | A61K 31/549 |
| WO | 2021119439 | 6/2021 | A61K 31/495 |

OTHER PUBLICATIONS

U.S. Appl. No. 18/373,208, filed Sep. 26, 2023, Park et al.
(Continued)

*Primary Examiner* — Savitha M Rao
(74) *Attorney, Agent, or Firm* — HAYES SOLOWAY P.C.

(57) ABSTRACT

A compound represented by Formula 1 according to the present disclosure, when used in combination with an anticancer drug, may significantly improve the anticancer effect of the anticancer drug, and may induce the same anticancer effect even when the anticancer drug is used in a significantly smaller amount than the conventionally used amount, thereby reducing the side effects caused by administration of the anticancer drug. Furthermore, the compound represented by Formula 1 makes it possible to effectively prevent, alleviate or treat either anticancer-resistant cancer or cancer which recurs or metastasizes after anticancer drug treatment.

13 Claims, 5 Drawing Sheets
(1 of 5 Drawing Sheet(s) Filed in Color)

(51) Int. Cl.

| | |
|---|---|
| *A61K 31/337* | (2006.01) |
| *A61K 31/395* | (2006.01) |
| *A61K 31/44* | (2006.01) |
| *A61K 31/475* | (2006.01) |
| *A61K 31/506* | (2006.01) |
| *A61K 31/513* | (2006.01) |
| *A61K 31/519* | (2006.01) |
| *A61K 31/5377* | (2006.01) |
| *A61K 31/704* | (2006.01) |
| *A61K 31/7068* | (2006.01) |
| *A61K 33/243* | (2019.01) |
| *A61K 38/17* | (2006.01) |
| *A61K 38/21* | (2006.01) |
| *A61K 39/395* | (2006.01) |
| *A61P 35/00* | (2006.01) |

(52) U.S. Cl.

CPC ............ *A61K 31/44* (2013.01); *A61K 31/475* (2013.01); *A61K 31/506* (2013.01); *A61K 31/513* (2013.01); *A61K 31/519* (2013.01); *A61K 31/5377* (2013.01); *A61K 31/5545* (2017.08); *A61K 31/704* (2013.01); *A61K 31/7068* (2013.01); *A61K 33/243* (2019.01); *A61K 38/179* (2013.01); *A61K 38/212* (2013.01); *A61K 39/3955* (2013.01); *A61P 35/00* (2018.01)

(58) Field of Classification Search

CPC .. A61K 31/475; A61K 31/506; A61K 31/513; A61K 31/519; A61K 31/5377; A61K 31/5545; A61K 31/555; A61K 31/704; A61K 31/7068; A61K 33/243; A61K 38/179; A61K 38/212; A61K 39/3955; A61P 35/00; C07D 471/04

See application file for complete search history.

(56) References Cited

U.S. PATENT DOCUMENTS

| | | | | |
|---|---|---|---|---|
| 2007/0197517 | A1 | 8/2007 | Jani et al. | 514/229.5 |
| 2009/0270625 | A1 | 10/2009 | Kajino et al. | 546/84 |
| 2010/0093691 | A1 | 4/2010 | Beck et al. | 514/210.16 |
| 2017/0056350 | A1 | 3/2017 | Haaga et al. | A61K 31/196 |
| 2018/0362525 | A1 | 12/2018 | Aguirre | A61P 35/02 |
| 2019/0328832 | A1 | 10/2019 | Coates | A61P 13/12 |
| 2022/0064171 | A1 | 3/2022 | Park | A61K 31/4985 |
| 2023/0137849 | A1 | 5/2023 | Fontenille et al. | A61K 31/549 |

OTHER PUBLICATIONS

U.S. Appl. No. 18/386,985, filed Nov. 3, 2023, Park et al.
Office Action issued in U.S. Appl. No. 18/373,208, dated Jun. 12, 2024, 13 pages.
BCCancer. Cisplatin. Retrieved from the Internet on Jun. 6, 2004, http://www.bccancer.bc.ca/drug-database-site.Drug%20Index/Cisplatin_monograph.pdf. Published Jul. 1, 2019. (Year: 2019), 11 pages.
Smith et al. The proteomic analysis of cisplatin resistance in breast cancer cells (Abstract). Oncol. Res. 2007; 16(11):497-506 (Year: 2007), 2 page.
International Search Report and Written Opinion issued in PCT/US22/41058, dated Nov. 21, 2022, 8 pages.
International Search Report and Written Opinion issued in PCT/US22/41059, dated Nov. 17, 2022, 8 pages.
"PubChem CID 2816010", Create date: Jul. 19, 2005, 11 pages.
St. Germain et al., "Cisplatin Induces Cytotoxicity through the Mitogen-Activated Protein Kinase Pathways and Activating Transcription Factor 3" *Neoplasia* vol. 12, No. 7, Jul. 2010, 527-538, 12 pages.
Turanli et al., "Discovery of therapeutic agents for prostate cancer using genome-scale metabolic modeling and drug repositioning" *EBioMedicine* 42, Mar. 21, 2019, 386-396 , 11 pages.
Glen et al., "Redefining adjuvant chemotherapy in patients with stage III colon cancer: X-ACT trial", 2008, Expert Rev. Anticancer Ther., 8(4), pp. 547-551. (001: 10.1586/14737140.8.4.547) (Year: 2008).
Lim et al., "Drug Discovery Using Evolutionary Similarities in Chemical Binding to Inhibit Patient-Derived Hepatocellular Carcinoma", 2022, Int. J. Mol. Sci., 23(14), Article:7971, pp. 1-21. https://doi.org/10.3390/ijms23147971) (Year: 2022).
Magne et al., "Oxaliplatin-5-Fluorouracil and Ionizing Radiation", 2003, Oncology, 64(3), pp. 280-287. (001: 10.1159/000069308) (Year: 2003).
Eloxatin, Prescribing Information, Sanofi-synthelabo, Oct. 2015, retrieved from CanerQuest on Dec. 6, 2022, 2022.
Noordhuis, P., Laan AC, van de Born K, Honeywell RJ, Peters GJ, Coexisting Moecular Determinants of Acquired Oxaliplatin Resistance in Human Colorectal and Ovarian Cancer Cell Lines. Int J. Mol Sci, Jul. 24, 2019; 20(15): 3619, 2019.
Gao et al., Antibiotics for cancer treatment: A double edged sword, Jn. of Cancer, Published Jun. 14, 2020.
Blondy et al. 5-Fluorouracil resistance mechanisms in colorectal cancer: From classical pathways to promising processes. Cancer Sci. Sep. 2020; 111(9):3142-3154. doi: 10.1111/cas.14532. Epub Aug. 13, 2020. (Year: 2020).
International Preliminary Report on Patentability issued in WO Patent Appln. No. PCT/US2022/041058, dated Feb. 27, 2024, 6 pgs.
International Preliminary Report on Patentability issued in WO Patent Appln. No. PCT/US2022/041059, dated Feb. 27, 2024, 6 pgs.

* cited by examiner

COMPOSITION FOR PREVENTING, ALLEVIATING OR TREATING CANCER

CROSS REFERENCE TO RELATED APPLICATION

The subject application is a divisional application of U.S. patent application Ser. No. 17/409,233, filed Aug. 23, 2021. The contents of which are disclosed herein in its entirety.

BACKGROUND

1. Technical Field

The present disclosure relates to a composition for preventing, alleviating or treating cancer.

2. Related Art

Cancer is a disease that contributes to a significant number of deaths worldwide, and cancer-related deaths worldwide in 2018 reached 9.6 million. In 1990s, cancer was the third leading cause of death, but in 2018, it ranked the second leading cause of death after heart diseases. Due to continued studies on cancer, the progression rate of cancer has decreased and the overall average survival rate has increased. Nevertheless, complete cure of cancer is still impossible due to resistance to anticancer drugs.

Anticancer drugs that are used in anticancer chemotherapy are drugs that inhibit the growth or proliferation of cancer cells. Anticancer drugs are roughly classified into cytotoxic anticancer drugs, targeted anticancer drugs, and immune anticancer drugs, and combination anticancer chemotherapy is also used in which anticancer drugs are selected depending the type or degree of progression of cancer, the patient's condition, etc. and two or more drugs are used simultaneously to increase the effects thereof. Cytotoxic anticancer drugs, known as first-generation anticancer drugs, exhibit anticancer effects by directly attacking cells that differentiate indiscriminately and rapidly. However, these cytotoxic anticancer drugs have the disadvantage of causing side effects such as decreased leukocytes, hair loss, vomiting, diarrhea, etc. because they also attack normal cells having the property of rapidly differentiating, such as hair follicle cells. Targeted anticancer drugs, known as second-generation anticancer drugs, act on specific protein or specific gene changes that appear in cancer cells, thus blocking signaling involved in cancer growth and differentiation. Unlike cytotoxic anticancer agents, these targeted anticancer agents have fewer side effects because they specifically act only on cancer cells without acting on normal cells.

However, one of the obstacles to the use of anticancer chemotherapy is the occurrence of anticancer drug resistance. In order for anticancer chemotherapy for cancer patients to be successful, cancer cells must be killed at a blood concentration at which normal tissues can survive. The expression "resistance to an anticancer drug" refers to a case in which cancer cells are not killed even when the anticancer drug is administered in an amount that can reach a blood concentration at which cancer cells can be killed. Anticancer drug resistance may vary from patient to patient and may even be induced by various factors including genetic differences between tumors derived from the same tissue. Cancer cell types derived from a single patient can acquire different genetic characteristics, and show not only diversity of gene expression but also activation of tumorinducing factors and inactivation of tumor suppressors, due to 'mutation'. As a result, all types of cancers express anticancer drug resistance genes in different patterns, and cells in a single cancer mass acquire diversity of drug resistance. In addition, even though tumors are not originally resistant to a specific anticancer therapy, once they are exposed to an anticancer drug, cells resistant to the anticancer drug selectively grow based on this diversity, and eventually many cancer cells rapidly have anticancer drug resistance. In this case, if a plurality of drugs targeting different intracellular substances are used, these drugs can effectively treat cancer, and increase the cure rate of cancer. In many cases, however, cells are simultaneously resistant to drugs that are structurally or functionally completely different. This phenomenon is known as multi-drug resistance (MDR) and is caused by limiting the intracellular accumulation of drugs through limited absorption or increased release of anticancer drugs, or changes in membrane lipids such as ceramides. Multi-drug resistance inhibits apoptosis induced by most anticancer drugs, causes DNA damage repair and drug detoxification, and further imparts anticancer drug resistance to cells by changing the cell cycle.

Therefore, there is a need to develop a new anticancer drug that can not only kill cancer cells, but also induce the death of cancer cells with anticancer drug resistance.

SUMMARY

An object of the present disclosure is to provide a composition for enhancing sensitivity to an anticancer drug or for co-administration with an anticancer drug.

Another object of the present disclosure is to provide a composition for overcoming or inhibiting anticancer drug resistance.

Still another object of the present disclosure is to provide a composition for preventing, alleviating or treating cancer.

However, objects to be achieved by the present disclosure are not limited to the above-mentioned objects, and other objects not mentioned herein will be clearly understood by those of ordinary skill in the art from the following description.

1. Composition

One embodiment of the present disclosure provides a composition for enhancing sensitivity to an anticancer drug or for co-administration with an anticancer drug.

The composition of the present disclosure contains, as an active ingredient, 1-(2-fluorophenyl)-4,6-dimethyl-1H,2H,3H-pyrrolo[3,2-c]quinoline represented by the following Formula 1 or a pharmaceutically acceptable salt thereof:

[Formula 1]

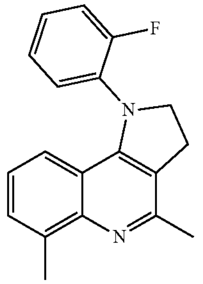

In the present disclosure, the CAS number of the compound represented by Formula 1 is 721884-42-0.

In the present disclosure, the pharmaceutically acceptable salt is a salt which is usually considered by those skilled in the art to be suitable for medical applications (e.g., because the salt is not harmful to a subject which may be treated with the salt), or a salt which gives rise to side effects which are tolerable within the respective treatment. Usually, the pharmaceutically acceptable salt is a salt which is considered as acceptable by the regulatory authorities, such as the US Food and Drug Administration (FDA), the European Medicines Agency (EMA), or the Japanese Ministry of Health, Labor and Welfare Pharmaceuticals and Medical Devices Agency (PMDA). However, the present disclosure in principle also encompasses salts of the compound according to the present disclosure which are as such not pharmaceutically acceptable, e.g. as intermediates in the production of the compound according to the present disclosure or physiologically functional derivatives thereof, or as intermediates in the production of pharmaceutically acceptable salts of the compound according to the present disclosure or physiologically functional derivatives thereof. The salts include water-insoluble salts and, particularly, water-soluble salts.

In each case, those skilled in the art can readily determine whether a certain compound according to the present disclosure or a physiologically functional derivative thereof can form a salt, i.e., whether the compound according to the present disclosure or a physiologically functional derivative thereof has a group which may carry a charge, such as an amino group, a carboxylic acid group, etc.

Exemplary salts of the compound of the present disclosure are acid addition salts or salts with bases, particularly pharmaceutically acceptable inorganic and organic acid addition salts and salts with bases commonly used in pharmacy, which are either water-insoluble or, particularly, water-soluble acid addition salts. Depending on the substituents of the compound of the present disclosure, salts with bases may also be suitable. Acid addition salts may, for example, be formed by mixing a solution of the compound of the present disclosure with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Likewise, pharmaceutically acceptable base addition salts may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, digluconate, dihydrochloride, dodecylsulfate, edetate, edisylate, ethanesulfonate, formate, fumarate, galactate, galacturonate, gluconate, glutamate, glycerophosphate, hemisulfate, heptanoate, hexanoate, hexylresorcinate, hydrobromide, hydrochloride, hydroiodide, 2-hydroxy-ethanesulfonate, hydroxynaphthoate, iodide, isobutyrate, isothionate, lactate, laurate, lauryl sulfate, malate, maleate, malonate, mandelate, methanesulfonate (mesylate), methylsulfate, 2-naphthalenesulfonate, nicotinate, nitrate, oleate, oxalate, palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, tosylate, undecanoate, valerate, and the like In the present disclosure, salts, which are not pharmaceutically acceptable and which can be obtained, for example, as process products during the production of the compound according to the present disclosure on an industrial scale, are also encompassed by the present disclosure and, if desired, may be converted into pharmaceutically acceptable salts by processes known to those skilled in the art.

The anticancer drug of the present disclosure may be an anticancer drug for preventing, alleviating or treating any one or more cancers selected from the group consisting of colorectal cancer, breast cancer, uterine cancer, fallopian tube cancer, ovarian cancer, stomach cancer, brain cancer, rectal cancer, small intestine cancer, esophageal cancer, lymph gland cancer, gallbladder cancer, lung cancer, skin cancer, kidney cancer, bladder cancer, blood cancer, pancreatic cancer, prostate cancer, thyroid cancer, endocrine adenocarcinoma, and oral cancer, for example, colorectal cancer, liver cancer or thyroid cancer, but is not limited thereto.

In the present disclosure, the cancer may be resistant cancer, recurrent cancer or metastatic cancer. With regard to the purposes of the present disclosure, the cancer may be cancer which is resistant to anticancer drug treatment or which has metastasized or recurred after anticancer drug treatment. Here, the anticancer drug is not particularly limited in kind and may be any kind of anticancer drug. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of cetuximab, panitumumab, irinotecan, vinorelbine, capecitabine, leucovorin, oxaliplatin, cisplatin, carboplatin, sorafenib, 5-fluorouracil (5-FU), bevacizumab, aflibercept and regorafenib, but is not limited thereto. More preferably, the anticancer drug may be, but is not limited to, FOLFOX regimen including 5-fluorouracil (5-FU), leucovorin (folinic acid) and oxaliplatin; FOLFIRI regimen including leucovorin (folinic acid), 5-fluorouracil (5-FU) and irinotecan; CAPDX regimen including capecitabine and oxaliplatin; oxaliplatin; or sorafenib.

The compound represented by Formula 1 according to the present disclosure may be co-administered with an anticancer drug to enhance the activity of the anticancer drug. In the present disclosure, the anticancer drug may include any drug whose activity may be enhanced by the compound represented by Formula 1 according to the present disclosure, thus preventing or treating cancer. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of paclitaxel, interferon alpha-2a, carboplatin, doxorubicin, cisplatin, gemcitabine, 5-fluorouracil, cetuximab, leucovorin, irinotecan, oxaliplatin, capecitabine, docetaxel, and sorafenib, but is not limited thereto.

In one example of the present disclosure, it was confirmed that, when the compound represented by Formula 1 was co-administered with at least one of oxaliplatin and sorafenib, which are anticancer drugs, it could effectively increase the activity of the anticancer drug against drug-resistant cancer, recurrent cancer or metastatic cancer, thus very effectively reducing the tumor volume and weight.

Another embodiment of the present disclosure provides a composition for overcoming or inhibiting anticancer drug resistance.

The composition of the present disclosure contains, as an active ingredient, 1-(2-fluorophenyl)-4,6-dimethyl-1H,2H,3H-pyrrolo[3,2-c]quinoline represented by Formula 1 above or a pharmaceutically acceptable salt thereof.

As used herein, the term "anticancer drug resistance" means that the effect of an anticancer drug decreases when the anticancer drug is used repeatedly in a certain amount. Specifically, the term "anticancer drug resistance" refers to a state in which the amount or frequency of use of an anticancer drug needs to be increased in order to obtain the same effect previously experienced in a patient with anticancer drug resistance, or a state in which the same effect as before is not obtained even when the anticancer drug is administered at the same dose as before. Here, the anticancer drug is not particularly limited in kind and may be any kind of anticancer drug. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of cetuximab, panitumumab, irinotecan, vinorelbine, capecitabine, leucovorin, oxaliplatin, cisplatin, carboplatin, sorafenib, 5-fluorouracil (5-FU), bevacizumab, aflibercept and regorafenib, but is not limited thereto. More preferably, the anticancer drug may be, but is not limited to, FOLFOX regimen including 5-fluorouracil (5-FU), leucovorin (folinic acid) and oxaliplatin; FOLFIRI regimen including leucovorin (folinic acid), 5-fluorouracil (5-FU) and irinotecan; CAPDX regimen including capecitabine and oxaliplatin; oxaliplatin; or sorafenib.

A used herein, the expression "overcoming or inhibiting anticancer drug resistance refers to an action of recovering from a state in which the effect of an anticancer drug decreases when the anticancer drug is used repeatedly in a certain amount, or the amount or frequency of use of an anticancer drug needs to be increased in order to obtain the same effect previously experienced in a patient with anticancer drug resistance, or a state in which the same effect as before is not obtained even when the anticancer drug is administered at the same dose as before. More specifically, the expression refers to an action of providing a state in which the same anticancer effect appears even if the anticancer drug is applied fewer times or at a smaller dose, or an action of returning to the state before the occurrence of anticancer drug resistance so that the same effect can be obtained even if the anticancer drug is administered at the same dose as before or at a lower dose.

The anticancer drug of the present disclosure may be an anticancer drug for preventing, alleviating or treating any one or more cancers selected from the group consisting of colorectal cancer, breast cancer, uterine cancer, fallopian tube cancer, ovarian cancer, stomach cancer, brain cancer, rectal cancer, small intestine cancer, esophageal cancer, lymph gland cancer, gallbladder cancer, lung cancer, skin cancer, kidney cancer, bladder cancer, blood cancer, pancreatic cancer, prostate cancer, thyroid cancer, endocrine adenocarcinoma, and oral cancer, for example, colorectal cancer, liver cancer or thyroid cancer, but is not limited thereto.

In one example of the present disclosure, it was confirmed that the compound represented by Formula 1 could overcome or inhibit resistance to at least one of oxaliplatin and sorafenib, which are anticancer drugs, thus effectively preventing, alleviating or treating anticancer drug-resistant cancer.

The description of the compound represented by Formula 1 and a pharmaceutically acceptable salt in the composition for overcoming or inhibiting anticancer drug resistance according to the present disclosure overlaps with that described above, and thus detailed description thereof will be omitted herein.

Still another embodiment of the present disclosure provides a composition for preventing, alleviating or treating cancer.

The composition of the present disclosure contains, as active ingredients: 1-(2-fluorophenyl)-4,6-dimethyl-1H,2H,3H-pyrrolo[3,2-c]quinoline represented by Formula 1 above or a pharmaceutically acceptable salt thereof; and an anticancer drug.

In the present disclosure, the anticancer drug may include any drug whose activity may be enhanced by the compound represented by Formula 1 according to the present disclosure, thus preventing or treating cancer. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of paclitaxel, interferon alpha-2a, carboplatin, doxorubicin, cisplatin, gemcitabine, 5-fluorouracil, cetuximab, leucovorin, irinotecan, oxaliplatin, capecitabine, docetaxel, and sorafenib, but is not limited thereto. More preferably, the anticancer drug may be at least one of oxaliplatin and sorafenib, but is not limited thereto.

In the composition of the present disclosure, the compound and the anticancer drug may be used at a ratio of 1:0.001 to 1:1,000, preferably 1:0.01 to 1:100, more preferably 1:0.1 to 1:10, but are not limited thereto. Here, the ratio may be a molar concentration ratio or a weight ratio, but is not limited thereto.

In the present disclosure, the cancer may be any one or more selected from the group consisting of colorectal cancer, breast cancer, uterine cancer, fallopian tube cancer, ovarian cancer, stomach cancer, brain cancer, rectal cancer, small intestine cancer, esophageal cancer, lymph gland cancer, gallbladder cancer, lung cancer, skin cancer, kidney cancer, bladder cancer, blood cancer, pancreatic cancer, prostate cancer, thyroid cancer, endocrine adenocarcinoma, and oral cancer, but is not limited thereto. For example, the cancer may be colorectal cancer, liver cancer or thyroid cancer, but is not limited thereto.

In the present disclosure, the cancer may be resistant cancer, recurrent cancer or metastatic cancer. With regard to the purposes of the present disclosure, the cancer may be cancer which is resistant to anticancer drug treatment or which has metastasized or recurred after treatment. Here, the anticancer drug is not particularly limited in kind and may be any kind of anticancer drug. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of cetuximab, panitumumab, irinotecan, vinorelbine, capecitabine, leucovorin, oxaliplatin, cisplatin, carboplatin, sorafenib, 5-fluorouracil (5-FU), bevacizumab, aflibercept and regorafenib, but is not limited thereto. More preferably, the anticancer drug may be, but is not limited to, FOLFOX regimen including 5-fluorouracil (5-FU), leucovorin (folinic acid) and oxaliplatin; FOLFIRI regimen including leucovorin (folinic acid), 5-fluorouracil (5-FU) and irinotecan; CAPDX regimen including capecitabine and oxaliplatin; oxaliplatin; or sorafenib.

In one example of the present disclosure, it was confirmed that, when the compound represented by Formula 1 was co-administered with an anticancer drug, preferably at least one of oxaliplatin and sorafenib, it was possible to effectively prevent, alleviate or treat cancer, particularly cancer resistant to at least one of oxaliplatin and sorafenib.

The description of the compound represented by Formula 1 and a pharmaceutically acceptable salt in the composition for preventing, alleviating or treating cancer according to the present disclosure overlaps with that described above, and thus detailed description thereof will be omitted herein.

As used herein, the term "prevention" or "preventing" refers to any action that inhibits or delays the onset of a disease or condition. With regard to the purposes of the present disclosure, the term means that the composition delays or inhibits the onset of cancer by being used together with an anticancer agent.

As used herein, the term "alleviation" or "alleviating" refers to any action that alleviates or beneficially changes disease or condition. With regard to the purposes of the present disclosure, the term means that the composition alleviates symptoms of cancer by being used together with an anticancer agent.

As used herein, the term "treatment" or "treating" refers to any action that delays, stops or reverses the progression of a disease or condition. With regard to the purposes of the present disclosure, the term means that the composition stops, alleviates, alleviates, abrogates or reverses the progression of cancer by being used together with an anticancer agent.

The composition of the present disclosure may be used as a pharmaceutical composition or a food composition, and the form thereof is not particularly limited.

The pharmaceutical composition of the present disclosure may be in the form of capsules, tablets, granules, injections, ointments, powders or beverages, and the pharmaceutical composition may be for human usage.

For use, the pharmaceutical composition of the present disclosure may be formulated in the form of, but not limited to, oral formulations, such as powders, granules, capsules, tablets or aqueous suspensions, as well as external preparations, suppositories, or sterile injectable solutions, according to the respective conventional methods. The pharmaceutical composition of the present disclosure may contain pharmaceutically acceptable carriers. Examples of the pharmaceutically acceptable carriers include a binder, a lubricant, a disintegrant, an excipient, a solubilizer, a dispersing agent, a stabilizer, a suspending agent, a dye, and a flavoring agent, which may be used for oral administration; a buffer, a preservative, an analgesic agent, a solubilizer, an isotonic agent, and a stabilizer, which may be used for injection; and a base, an excipient, a lubricant, and a preservative, which may be used for topical administration.

The formulation of the pharmaceutical composition of the present disclosure may be prepared in various ways by mixing with pharmaceutically acceptable carriers as described above. For example, for oral administration, the pharmaceutical composition may be prepared in the form of tablets, troches, capsules, elixir, suspensions, syrups, wafers, or the like, and for injection, the pharmaceutical composition may be prepared as a unit dosage ampoule or a multiple-dosage form. In addition, the pharmaceutical composition may be formulated as solutions, suspensions, tablets, capsules, sustained-release formulations, or the like.

Examples of carriers, excipients and diluents suitable for the formulation of the present disclosure include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition of the present disclosure may further contain a filler, an anticoagulant, a lubricant, a wetting agent, a fragrance, an emulsifier, a preservative, etc.

The routes of administration of the pharmaceutical composition according to the present disclosure include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred.

In the present disclosure, "parenteral" includes subcutaneous, transdermal, intravenous, intramuscular, intra-articular, intra-synovial, intrasternal, intradural, intra-lesional and intra-cranial injection or infusion techniques. The pharmaceutical composition of the present disclosure may also be formulated as suppositories for intrarectal administration.

The pharmaceutical composition of the present disclosure may vary depending on various factors, including the activity of a specific compound used, the patient's age, body weight, general health, sex and diet, the period of administration, the route of administration, excretion rate, the drug content, and the severity of a specific disease to be prevented or treated. The dose of the pharmaceutical composition may be suitably selected by a person skilled in the art depending on the patient's condition and body weight, the severity of the disease, the form of drug, and the route and period of administration, and may be 0.0001 to 50 mg/kg/day or 0.001 to 50 mg/kg/day. The pharmaceutical composition may be administered once or several times a day. The dose is not intended to limit the scope of the present disclosure in any way. The pharmaceutical composition according to the present disclosure may be formulated as pills, sugar-coated tablets, capsules, liquids, gels, syrups, slurries, or suspensions.

The food composition of the present disclosure may be prepared in the form of various foods, for example, beverages, gums, teas, vitamin complexes, powders, granules, tablets, capsules, confectionery, rice cakes, or bread.

When the compound represented by Formula 1 according to the present disclosure is contained as an active ingredient in the food composition, it may be added in an amount of 0.1 to 50 wt % based on the total weight of the food composition, but is not limited thereto.

When the food composition of the present disclosure is prepared as a beverage, there is no particular limitation, except that the beverage contains the food composition at the indicated percentage. The beverage may additionally contain various flavorings or natural carbohydrates, like conventional beverages. Specifically, examples of the natural carbohydrates include monosaccharides such as glucose, disaccharides such as fructose, polysaccharides such as sucrose, conventional sugars such as dextrin, cyclodextrin or the like, and sugar alcohols such as xylitol, sorbitol, erythritol or the like. Examples of the flavorings include natural flavorings (thaumatin, stevia extracts, such as rebaudioside A, glycyrrhizin, etc.) and synthetic flavorings (saccharin, aspartame, etc.).

The food composition of the present disclosure may further contain various nutrients, vitamins, minerals (electrolytes), flavorings such as synthetic flavorings and natural flavorings, colorants, pectic acid and its salt, alginic acid and its salt, organic acids, protective colloidal thickeners, pH adjusting agents, stabilizers, preservatives, glycerin, alcohol, carbonizing agents as used in carbonated beverages, etc.

The ingredients that are contained in the food composition of the present disclosure may be used independently or in combination. The proportion of the additives is not critical to the present disclosure, but may be selected in a range of 0.1 to about 50 parts by weight per 100 parts by weight of the food composition of the present disclosure, but is not limited thereto.

2. Method

According to another embodiment of the present disclosure, the present disclosure is directed to a method for overcoming or inhibiting anticancer drug resistance or enhancing sensitivity to an anticancer drug.

The method of the present disclosure may comprise a step of administering an effective amount of 1-(2-fluorophenyl)-4,6-dimethyl-1H,2H,3H-pyrrolo[3,2-c]quinoline represented by Formula 1 above or a pharmaceutically acceptable salt thereof to a subject in need of administration.

The anticancer drug of the present disclosure may be an anticancer drug for preventing, alleviating or treating any one or more cancers selected from the group consisting of colorectal cancer, breast cancer, uterine cancer, fallopian tube cancer, ovarian cancer, stomach cancer, brain cancer, rectal cancer, small intestine cancer, esophageal cancer, lymph gland cancer, gallbladder cancer, lung cancer, skin cancer, kidney cancer, bladder cancer, blood cancer, pancreatic cancer, prostate cancer, thyroid cancer, endocrine adenocarcinoma, and oral cancer, for example, colorectal cancer, liver cancer or thyroid cancer, but is not limited thereto.

In the present disclosure, the cancer may be resistant cancer, recurrent cancer or metastatic cancer. With regard to the purposes of the present disclosure, the cancer may be cancer which is resistant to anticancer drug treatment or which has metastasized or recurred after treatment. Here, the anticancer drug is not particularly limited in kind and may be any kind of anticancer drug. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of cetuximab, panitumumab, irinotecan, vinorelbine, capecitabine, leucovorin, oxaliplatin, cisplatin, carboplatin, sorafenib, 5-fluorouracil (5-FU), bevacizumab, aflibercept and regorafenib, but is not limited thereto. More preferably, the anticancer drug may be, but is not limited to, FOLFOX regimen including 5-fluorouracil (5-FU), leucovorin (folinic acid) and oxaliplatin; FOLFIRI regimen including leucovorin (folinic acid), 5-fluorouracil (5-FU) and irinotecan; CAPDX regimen including capecitabine and oxaliplatin; oxaliplatin; or sorafenib.

The compound represented by Formula 1 according to the present disclosure may be co-administered with an anticancer drug to enhance the activity of the anticancer drug. In the present disclosure, the anticancer drug may include any drug whose activity may be enhanced by the compound represented by Formula 1 according to the present disclosure, thus preventing or treating cancer. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of paclitaxel, interferon alpha-2a, carboplatin, doxorubicin, cisplatin, gemcitabine, 5-fluorouracil, cetuximab, leucovorin, irinotecan, oxaliplatin, capecitabine, docetaxel, and sorafenib.

The description of the compound represented by Formula 1 and a pharmaceutically acceptable salt in the method for overcoming or inhibiting anticancer drug resistance or enhancing sensitivity to an anticancer drug according to the present disclosure overlaps with that described above, and thus detailed description thereof will be omitted herein.

According to another embodiment of the present disclosure, the present disclosure is directed to a method for preventing, alleviating or treating cancer.

The method of the present disclosure may comprise a step of administering, to a subject in need of administration, an effective amount of 1-(2-fluorophenyl)-4,6-dimethyl-1H,2H,3H-pyrrolo[3,2-c]quinoline represented by Formula 1 above or a pharmaceutically acceptable salt thereof and an effective amount of an anticancer drug.

In the present disclosure, the anticancer drug may include any drug whose activity may be enhanced by the compound represented by Formula 1 according to the present disclosure, thus preventing or treating cancer. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of paclitaxel, interferon alpha-2a, carboplatin, doxorubicin, cisplatin, gemcitabine, 5-fluorouracil, cetuximab, leucovorin, irinotecan, oxaliplatin, capecitabine, docetaxel, and sorafenib, but is not limited thereto. More preferably, the anticancer drug may be at least one of oxaliplatin and sorafenib, but is not limited thereto.

In the method of the present disclosure, the compound and the anticancer drug may be used at a ratio of 1:0.001 to 1:1,000, preferably 1:0.01 to 1:100, more preferably 1:0.1 to 1:10, but are not limited thereto. Here, the ratio may be a molar concentration ratio or a weight ratio, but is not limited thereto.

In the present disclosure, the cancer may be any one or more selected from the group consisting of colorectal cancer, breast cancer, uterine cancer, fallopian tube cancer, ovarian cancer, stomach cancer, brain cancer, rectal cancer, small intestine cancer, esophageal cancer, lymph gland cancer, gallbladder cancer, lung cancer, skin cancer, kidney cancer, bladder cancer, blood cancer, pancreatic cancer, prostate cancer, thyroid cancer, endocrine adenocarcinoma, and oral cancer, but is not limited thereto. For example, the cancer may be colorectal cancer, liver cancer or thyroid cancer, but is not limited thereto.

In the present disclosure, the cancer may be resistant cancer, recurrent cancer or metastatic cancer. With regard to the purposes of the present disclosure, the cancer may be a cancer which is resistant to anticancer drug treatment or which has metastasized or recurred after anticancer drug treatment. Here, the anticancer drug is not particularly limited in kind and may be any kind of anticancer drug. For example, the anticancer drug may be at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine, but is not limited thereto. Preferably, the anticancer drug may be at least one selected from the group consisting of cetuximab, panitumumab, irinotecan, vinorelbine, capecitabine, leucovorin, oxaliplatin, cisplatin, carboplatin, 5-fluorouracil (5-FU), bevacizumab, aflibercept and regorafenib, but is not limited thereto. More preferably, the anticancer drug may be, but is not limited to, FOLFOX regimen including 5-fluorouracil (5-FU), leucovorin (folinic acid) and oxaliplatin; FOLFIRI regimen including leucovorin (folinic acid), 5-fluorouracil (5-FU) and irinotecan; CAPDX regimen including capecitabine and oxaliplatin; oxaliplatin; or sorafenib.

The description of the compound represented by Formula 1 and a pharmaceutically acceptable salt in the method for preventing, alleviating or treating cancer according to the present disclosure overlaps with that described above, and thus detailed description thereof will be omitted herein.

As used herein, the term "administering" refers to providing the composition of the present disclosure to a subject by any suitable method.

As used herein, the term "subject" in need of administration may include mammals and non-mammals Here, examples of the mammals include, but are not limited to, humans, non-human primates such as chimpanzees, other ape or monkey species; livestock animals such as cattle, horses, sheep, goats or pigs; domestic animals such as rabbits, dogs or cats; laboratory animals such as rodents, for example, rats, mice or guinea pigs. In addition, in the present disclosure, examples of the non-mammal may include, but are not limited to, birds or fish.

In the present disclosure, the formulation of the composition that is administered as described above is not particularly limited. The composition may be administered as a solid formulation, a liquid formulation, or an aerosol formulation for inhalation. In addition, the composition may be administered as a solid formulation which is intended to be converted into a liquid formulation for oral or parenteral administration immediately prior to use. For example, the composition may be formulated and administered in the form of, but not limited to, oral formulations, such as powders, granules, capsules, tablets or aqueous suspensions, as well as external preparations, suppositories, or sterile injectable solutions.

In addition, in the present disclosure, pharmaceutically acceptable carriers may be additionally administered together with the composition of the present disclosure during administration. Examples of the pharmaceutically acceptable carriers include a binder, a lubricant, a disintegrant, an excipient, a solubilizer, a dispersing agent, a stabilizer, a suspending agent, a dye, and a flavoring agent, which may be used for oral administration; a buffer, a preservative, an analgesic agent, a solubilizer, an isotonic agent, and a stabilizer, which may be used for injection; and a base, an excipient, a lubricant, and a preservative, which may be used for topical administration. The formulation of the compound of the present disclosure may be prepared in various ways by mixing with pharmaceutically acceptable carriers as described above. For example, for oral administration, the composition may be prepared in the form of tablets, troches, capsules, elixir, suspensions, syrups, wafers, or the like, and for injection, the composition may be prepared as a unit dosage ampoule or a multiple-dosage form. In addition, the composition may be formulated as solutions, suspensions, tablets, capsules, sustained-release formulations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the composition may further contain a filler, an anticoagulant, a lubricant, a wetting agent, a fragrance, an emulsifier, a preservative, or the like.

The routes of administration of the composition according to the present disclosure include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred.

In the present disclosure, "parenteral" includes subcutaneous, transdermal, intravenous, intramuscular, intra-articular, intra-synovial, intrasternal, intradural, intra-lesional and intra-cranial injection or infusion techniques. The pharmaceutical composition of the present disclosure may also be formulated as suppositories for intrarectal administration.

As used herein, the term "pharmaceutically effective amount" refers to a sufficient amount of an agent to provide a desired biological result. The result may be the reduction and/or alleviation of the signs, symptoms, or causes of a disease, or any other desired alteration of a biological system. For example, an "effective amount" for therapeutic uses is the amount of the composition disclosed in the present disclosure, which is required to provide a clinically significant decrease in a disease. An appropriate "effective amount" in any individual case may be determined by one skilled in the art using routine experimentation. Accordingly, the expression "effective amount" generally refers to an amount in which the active substance has a therapeutic effect. In the present disclosure, the active substance is an agent for preventing, alleviating or treating cancer while being an agent for preventing, alleviating or treating anticancer drug-resistant cancer.

The composition of the present disclosure may vary depending on various factors, including the activity of an active substance used, the patient's age, body weight, general health, sex and diet, the period of administration, the route of administration, excretion rate, the drug content, and the severity of a specific disease to be prevented or treated. The dose of the active substance may be suitably selected by a person skilled in the art depending on the patient's condition and body weight, the severity of the disease, the form of drug, and the route and period of administration, and may be 0.0001 to 100 mg/kg/day or 0.001 to 100 mg/kg/day. The active substance may be administered once or several times a day. The dose is not intended to limit the scope of the present disclosure in any way. The compound according to the present disclosure may be formulated as pills, sugar-coated tablets, capsules, liquids, gels, syrups, slurries, or suspensions.

The active substance of the present disclosure may be used alone or in combination with methods that use surgery, radiotherapy, hormone therapy, chemotherapy, and biological response modifiers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Hereinafter, the present disclosure will be described in detail with reference to the following examples. However, the following examples are only illustrative of the present disclosure, and the scope of the present disclosure is not limited by the following examples.

EXAMPLES

[Example 1] Isolation of Cancer Cells from Cancer Patients Who have Relapsed after Anticancer Drug Treatment Cancer cells were isolated from patients with colorectal cancer, liver cancer, and thyroid cancer as described in Table 1 below, who have relapsed after anticancer drug treatment.

TABLE 1

| | Patient 1 (YUMC-C1 cell line) | Patient 2 (YUMC-H2 cell line) | Patient 3 (YUMC-P1 cell line) |
|---|---|---|---|
| Age | 71 | 71 | 57 |
| Sex | Female | Male | Male |
| Location of primary disease | Colon | Liver | Thyroid |
| Stage | IVc | IVc | IVc |
| Primary pathology | Colorectal cancer (recurred and metastasized after FOLFOX*) | Liver cancer (recurred after sorafenib) | Thyroid papillary cancer (recurred after sorafenib) |
| Classification of samples used in culture | Fresh tumor | Fresh tumor | Fresh tumor |
| Source | Severance Hospital (Seoul, Korea) | Severance Hospital (Seoul, Korea) | Severance Hospital (Seoul, Korea) |

*FOLFOX: Triple co-administration of Folinic acid, 5-Fluorouracil (5-FU) and Oxaliplatin in colorectal cancer

[Example 2] Analysis of Gene Expression by Microarray

Using the microarray analysis method, gene expression was compared between the YUMC-C1 cell line, YUMC-H2 cell line and YUMC-P1 cell line of Example 1, and a control group which is the thyroid cancer cell line (YUMC-M1) isolated from a thyroid cancer patient who had successfully undergone anticancer therapy by administration of an anticancer drug for standard anticancer therapy.

Figure 1:
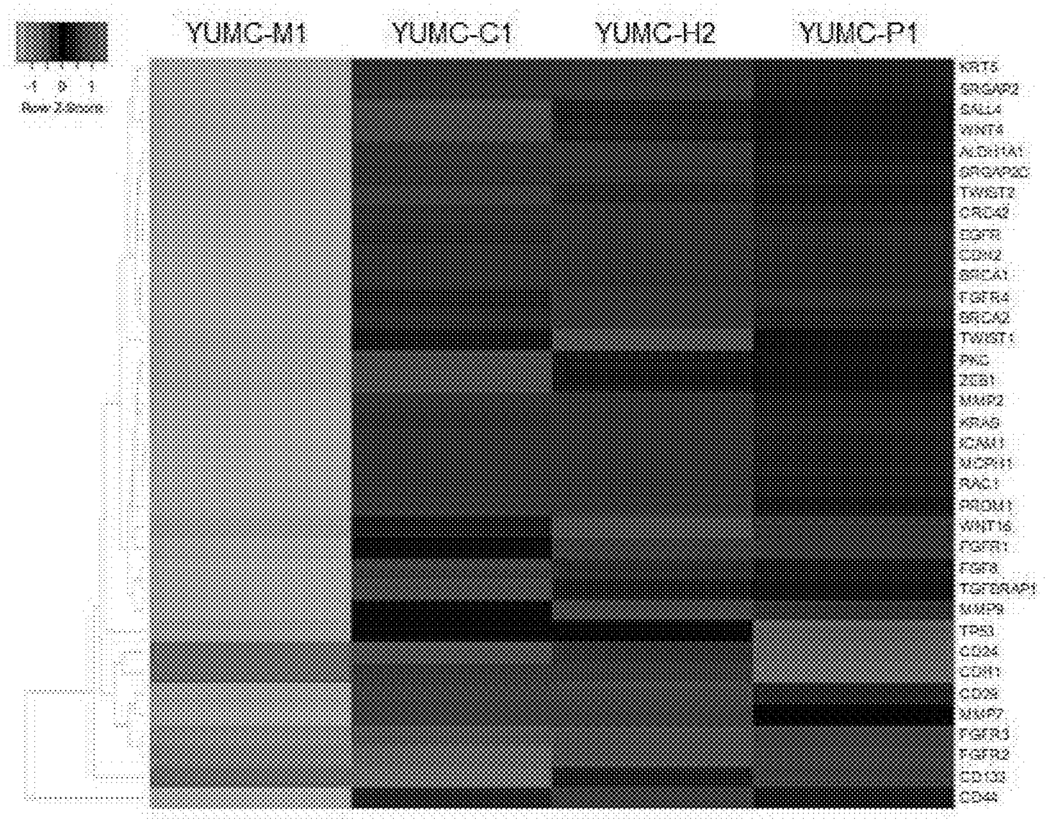
FIG. 1 shows the results of microarray analysis performed to analyze gene expression changes in YUMC-C1, YUMC-H2 and YUMC-P1 cell lines according to one example of the present disclosure.

Specifically, RNA purity and integrity were measured using an ND-1000 spectrophotometer (NanoDrop) and an Agilent 2100 Bioanalyzer (Agilent Technologies). RNA labeling and hybridization was performed using an Agilent One-Color Microarray-Based Gene Expression Analysis protocol (Agilent Technology, V 6.5, 2010). 100 ng of total RNA from each sample was amplified linearly and labeled with Cy3-dCTP, and the labeled cRNA was purified using an RNeasy Mini Kit (Qiagen). The concentration and specific activity of the labeled cRNA (pmol Cy3/ng cRNA) were measured using NanoDrop ND-1000. Then, 600 ng of each labeled cRNA was fragmented by adding 5 μl of 10× blocking agent and 1 μl of 25× fragmentation buffer, followed by heating at 60° C. for 30 minutes. Finally, 25 μl of 2× GE hybridization buffer was added to dilute the labeled cRNA. 40 μl of hybridization solution was dispensed into a gasket slide and assembled to the Agilent SurePrint G3 Human GE 8X60K V3 Microarrays (Agilent®). Raw data were extracted using Agilent Feature Extraction Software (v11.0.1.1), and then the raw data for each gene were summarized in the Agilent feature extraction protocol to generate a raw data text file, thus providing expression information for each gene. Gene-enrichment and functional annotation analysis for the significant probe list was performed using gene ontology and Kyoto Encyclopedia for Genes and Genomes (KEGG) analyses. All data analysis and visualization of differentially expressed genes were conducted using R 3.1.2. FIG. 1 shows the results of analyzing the differentially expressed genes.

As shown in FIG. 1, it could be confirmed that the expression levels of genes corresponding to cancer stem cell markers significantly increased in the YUMC-C1, YUMC-H2 and YUMC-P1 cell lines that are anticancer drug-resistant cancer cells, compared to the gene expression levels in the YUMC-M1 cell line which is a non-anticancer drug-resistant cancer cell line.

Through these results, it can be seen that the YUMC-C1, YUMC-H2 and YUMC-P1 cell lines of the present disclosure are cancer stem cells having anticancer drug resistance.

Figure 2:
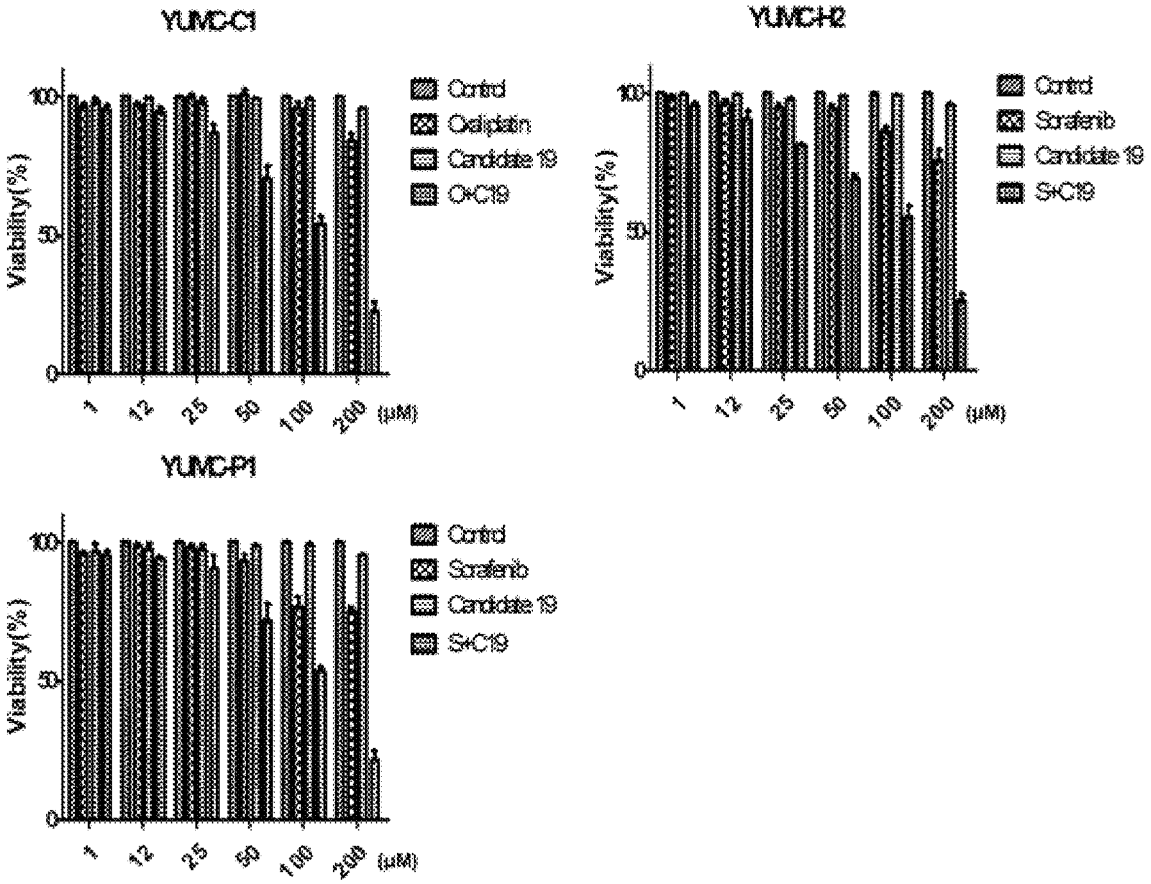
FIG. 2 graphically shows the results of measuring the changes in cell viability after treating YUMC-C1, YUMC-H2 and YUMC-P1 cell lines with drugs according to one example of the present disclosure.

[Example 3] Results of Evaluating the Effect of Killing Anticancer Drug-Resistant Cancer Cells Lines Each of the YUMC-C1, YUMC-H2 and YUMC-P1 cell lines of Example 1 was inoculated into 96-well plates at a density of $6\times10^3$ cells/well and then cultured overnight to a confluence of 90%. After 1-(2-fluorophenyl)-4,6-dimethyl-1H,2H,3H-pyrrolo[3,2-c]quinoline (Candidate 19) represented by Formula 1 and oxaliplatin or sorafenib were added to final concentrations of 0 to 200 μM, the cells were cultured. However, when 1-(2-fluorophenyl)-4,6-dimethyl-1H,2H,3H-pyrrolo[3,2-c]quinoline was used in combination with oxaliplatin or sorafenib, the treatment concentration of each of oxaliplatin and sorafenib was 30 μM. Thereafter, cell viability was measured using the MTT reagent. The absorbance was measured at 550 nm, and viable cells were counted using trypan blue staining. FIG. 2 graphically shows the change in cell viability after each treatment, and Table 2 below shows the $IC_{50}$ value when treated with 1-(2-fluorophenyl)-4,6-dimethyl-1H,2H,3H-pyrrolo[3,2-c]quinoline in combination with oxaliplatin or sorafenib.

TABLE 2

| | $IC_{50}$ (μM) | | |
|---|---|---|---|
| | YUMC-C1 cell line | YUMC-H2 cell line | YUMC-P1 cell line |
| Candidate 19 + oxaliplatin | 120 | — | — |
| Candidate 19 + sorafenib | — | 120 | 120 |

As shown in FIG. 2, it could be confirmed that, even when the YUMC-C1 cell line was treated with oxaliplatin at a high concentration of 200 μM, more than 80% of the cells survived, and even when the treatment concentration of sorafenib for the YUMC-H2 and YUMC-P1 cell lines was increased to 200 μM, more than 80% of the cells also survived, suggesting that the cell lines showed high resistance to these anticancer drugs. However, it could be confirmed that, when each of the above-described cell lines was treated with 1-(2-fluorophenyl)-4,6-dimethyl-1H,2H,3H- pyrrolo[3,2-c]quinoline in combination with oxaliplatin or sorafenib, the death rate of the cancer cells significantly increased. In addition, as shown in Table 2 above, the $IC_{50}$ concentrations of 1-(2-fluorophenyl)-4,6-dimethyl-1H,2H,3H-pyrrolo[3,2-c]quinoline (Candidate 19) plus standard anticancer drug (oxaliplatin or sorafenib) for the anticancer drug-resistant YUMC-C1, YUMC-H2 and YUMC-P1 cell lines were low at 120 μM, 120 μM and 120 μM, respectively.

Figure 3:
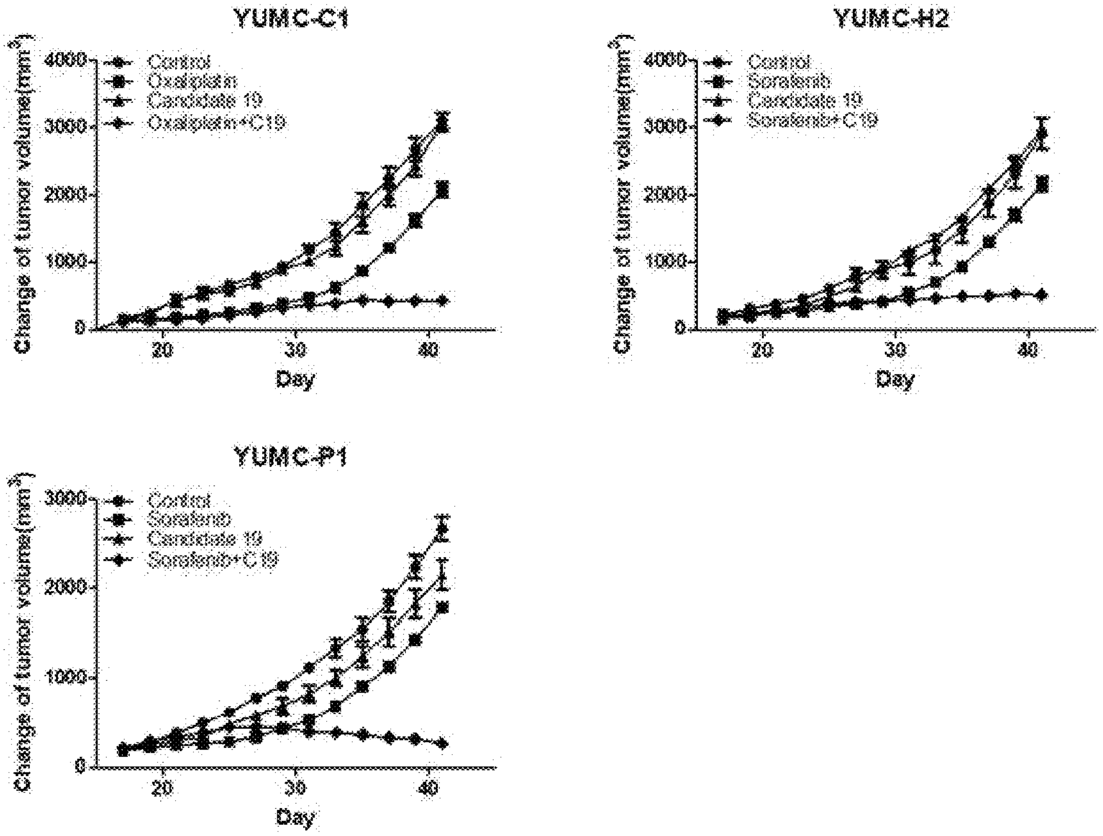
FIG. 3 graphically shows the results of measuring the changes in tumor size after administering drugs to mouse models xenografted with YUMC-C1, YUMC-H2 and YUMC-P1 cell lines, respectively, according to one example of the present disclosure.
Figure 4:
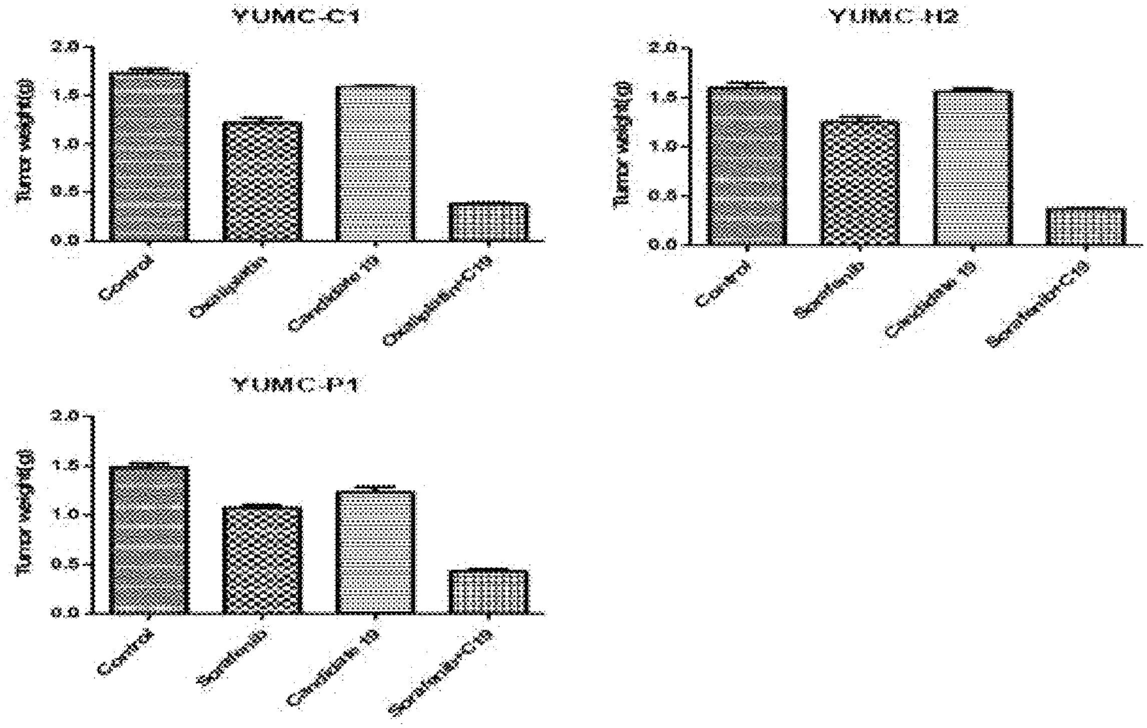
FIG. 4 graphically shows the results of measuring the changes in net tumor weight after administering drugs to mouse models xenografted with YUMC-C1, YUMC-H2 and YUMC-P1 cell lines, respectively, according to one example of the present disclosure.
Figure 5:
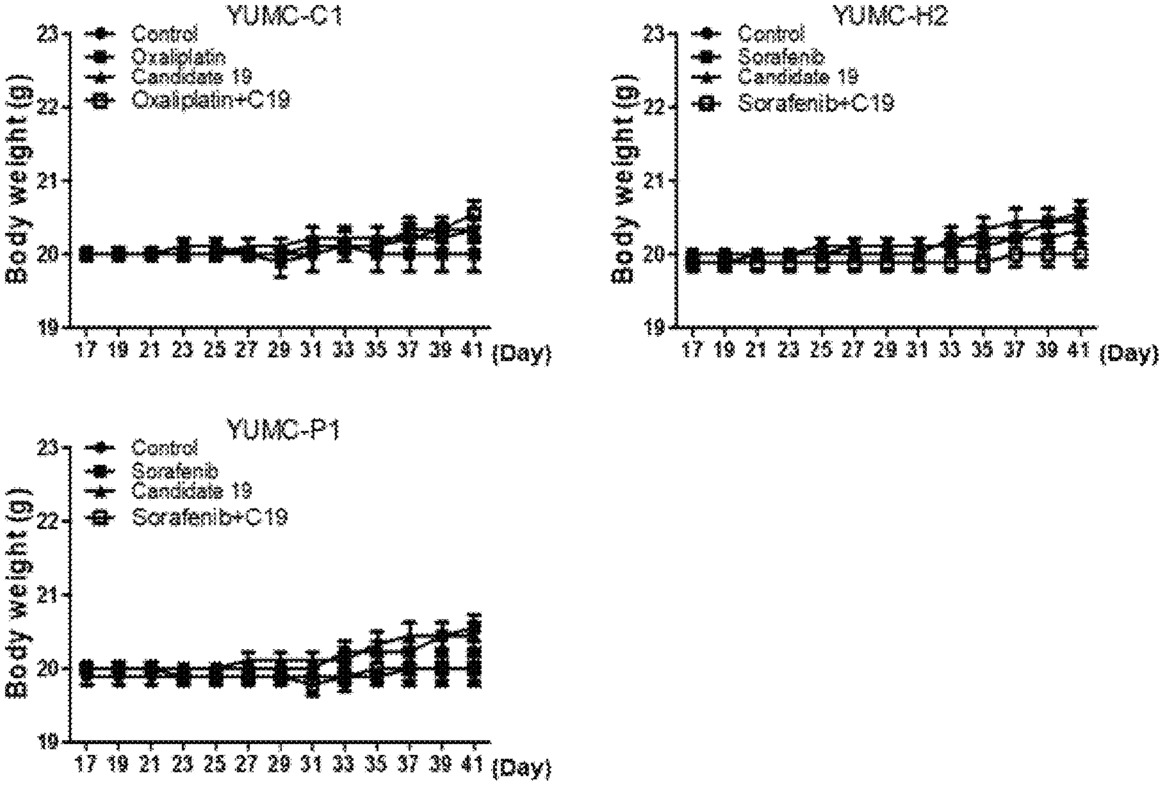
FIG. 5 graphically shows the results of measuring the changes in mouse body weight after administering drugs to mouse models xenografted with YUMC-C1, YUMC-H2 and YUMC-P1 cell lines, respectively, according to one example of the present disclosure.

[Example 4] Results of Evaluating Therapeutic Effect in Mouse Models Xenografted with Anticancer Drug-Resistant Cancer Cell Lines Each of the YUMC-C1, YUMC-H2 and YUMC-P1 cell lines ($4.5\times10^6$ cells/mouse) of Example 1 was cultured in test tubes and then was subcutaneously injected into the upper left flank regions of 6-week-old female BALB/c nude, NOD/Shi-scid, IL-2Rγ KOJic (NOG) mice. 15 days after injection of each of the cell lines, when the tumor volume reached about 100 to 200 $mm^3$, mice having a tumor with the above volume were randomly grouped (n=10/group), and then each drug was administered to the mice 13 times for a total of 41 days under the conditions shown in Table 3 below. Then, the changes in tumor volume during this administration were measured, and the results of the measurement are shown in FIG. 3. In addition, the tumor was extracted and the net weight of the tumor was measured, and the results of the measurement are shown in FIG. 4. In addition, changes in the body weights of the mice were measured, and the results of the measurement are shown in FIG. 5. Here, nothing was administered to the control group.

TABLE 3

| | Administration conditions |
|---|---|
| Group 1 | — |
| Group 2 | Oxaliplatin (17 mg/kg) alone, oral administration |
| Group 3 | Sorafenib (80 mg/kg) alone, oral administration |
| Group 4 | 1-(2-fluorophenyl)-4,6-dimethyl-1H,2H,3H-pyrrolo[3,2-c]quinoline (25 mg/kg, Candidate 19) represented by Formula 1 alone, oral administration |
| Group 5 | Oxaliplatin (8.5 mg/kg), oral administration<br>1-(2-fluorophenyl)-4,6-dimethyl-1H,2H,3H-pyrrolo[3,2-c]quinoline (25 mg/kg, Candidate 19), oral administration |
| Group 6 | Sorafenib (25 mg/kg), oral administration<br>1-(2-fluorophenyl)-4,6-dimethyl-1H,2H,3H-pyrrolo[3,2-c]quinoline (25 mg/kg, Candidate 19), oral administration |

As shown in FIGS. 3 and 4, when oxaliplatin was administered to the mouse model xenografted with the YUMC-C1 cell line, the mouse model showed anticancer drug resistance compared to the control group, and thus the volume and weight of the tumor did not significantly decrease. In addition, even when sorafenib was administered to the mouse models xenografted with the YUMC-H2 and YUMC-P1 cell lines, no significant changes in the tumor volume and weight were observed. However, it could be confirmed that, when 1-(2-fluorophenyl)-4,6-dimethyl-1H,2H,3H-pyrrolo[3,2-c]quinoline (Candidate 19) represented by Formula 1, together with the anticancer drug oxaliplatin or sorafenib, was administered to these mouse models, the tumor volume and weight significantly decreased.

Meanwhile, as shown in FIG. 5, it could be confirmed that, when 1-(2-fluorophenyl)-4,6-dimethyl-1H,2H,3H-pyrrolo[3,2-c]quinoline represented by Formula 1 was administered alone or in combination with the anticancer drug oxaliplatin or sorafenib to the mouse models xenografted with the YUMC-C1, YUMC-H2 and YUMC-P1 cell lines, there was no changes in the body weights of all the mice, suggesting that there was no toxicity problem.

Through the above results, it can be seen that, when the 1-(2-fluorophenyl)-4,6-dimethyl-1H,2H,3H-pyrrolo[3,2-c]quinoline compound represented by Formula 1 according to the present disclosure is used in combination with an anticancer drug against various kinds of cancers showing resistance to the anticancer drug, it can not only significantly improve the anticancer effect of the anticancer drug, but also can induce the same anticancer effect even when the anticancer drug is used in a significantly smaller amount than the conventionally used amount, thereby reducing the side effects caused by administration of the anticancer drug.

As described above, the compound represented by Formula 1, when used in combination with an anticancer drug, can significantly improve the anticancer effect of the anticancer drug, and can induce the same anticancer effect even when the anticancer drug is used in a significantly smaller amount than the conventionally used amount, thereby reducing the side effects caused by administration of the anticancer drug. Furthermore, the compound represented by Formula 1 makes it possible to effectively prevent, alleviate or treat either anticancer-resistant cancer or cancer recurs or metastasizes after anticancer drug treatment.

What is claimed is:

1. A pharmaceutical composition for enhancing sensitivity to an anticancer drug or for co-administration with the anticancer drug, the pharmaceutical composition containing, as an active ingredient, 1-(2-fluorophenyl)-4,6-dimethyl-1H,2H,3H-pyrrolo[3,2-c]quinoline represented by the following Formula 1 or a pharmaceutically acceptable salt thereof:

[Formula 1]

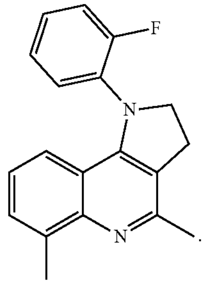

2. The pharmaceutical composition of claim 1, wherein the anticancer drug is an anticancer drug for preventing, alleviating or treating any one or more cancers selected from the group consisting of colorectal cancer, breast cancer, uterine cancer, fallopian tube cancer, ovarian cancer, stomach cancer, brain cancer, rectal cancer, small intestine cancer, esophageal cancer, lymph gland cancer, gallbladder cancer, lung cancer, skin cancer, kidney cancer, bladder cancer, blood cancer, pancreatic cancer, prostate cancer, thyroid cancer, endocrine adenocarcinoma, oral cancer, and liver cancer.

3. The pharmaceutical composition of claim 1, wherein the anticancer drug is at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine.

4. The pharmaceutical composition of claim 3, wherein the anticancer drug is at least one selected from the group consisting of cetuximab, panitumumab, irinotecan, vinorelbine, capecitabine, leucovorin, oxaliplatin, cisplatin, carboplatin, sorafenib, 5-fluorouracil (5-FU), bevacizumab, aflibercept, and regorafenib.

5. A pharmaceutical composition for overcoming or inhibiting anticancer drug resistance, the pharmaceutical composition containing, as an active ingredient, 1-(2-fluorophenyl)-4,6-dimethyl-1H,2H,3H-pyrrolo[3,2-c]quinoline represented by the following Formula 1 or a pharmaceutically acceptable salt thereof:

[Formula 1]

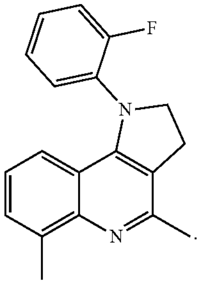

6. The pharmaceutical composition of claim 5, wherein the anticancer drug is an anticancer drug for preventing, alleviating or treating any one or more cancers selected from the group consisting of colorectal cancer, breast cancer, uterine cancer, fallopian tube cancer, ovarian cancer, stomach cancer, brain cancer, rectal cancer, small intestine cancer, esophageal cancer, lymph gland cancer, gallbladder cancer, lung cancer, skin cancer, kidney cancer, bladder cancer, blood cancer, pancreatic cancer, prostate cancer, thyroid cancer, endocrine adenocarcinoma, oral cancer, and liver cancer.

7. The pharmaceutical composition of claim 5, wherein the anticancer drug is at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine.

8. A pharmaceutical composition for preventing or treating cancer, the pharmaceutical composition containing, active ingredients: 1-(2-fluorophenyl)-4,6-dimethyl-1H,2H,3H-pyrrolo[3,2-c]quinoline represented by the following Formula 1 or a pharmaceutically acceptable salt thereof; and an anticancer drug:

[Formula 1]

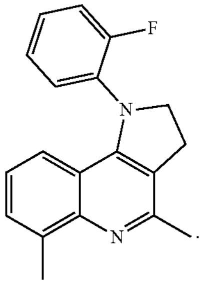

9. The pharmaceutical composition of claim 8, wherein the anticancer drug is at least one selected from the group consisting of nitrogen mustard, imatinib, oxaliplatin, rituximab, panitumumab, erlotinib, neratinib, lapatinib, gefitinib, vandetanib, nirotinib, semaxanib, bosutinib, axitinib, cediranib, lestaurtinib, sorafenib, lenvatinib, trastuzumab, gefitinib, bortezomib, sunitinib, carboplatin, 5-fluorouracil (5-FU), bevacizumab, cisplatin, cetuximab, aflibercept, regorafenib, viscumalbum, asparaginase, tretinoin, hydroxycarbamide, dasatinib, estramustine, gemtuzumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, leucovorine, carmofur, raltitrexed, interferon alpha-2a, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temsirolimus, temozolomide, busulfan, ifosfamide, cyclophosphamide, melphalan, altretamine, dacabazine, thiotepa, nimustine, chlorambucil, mitolactol, leucovorin, tretonin, exemestane, aminoglutethimide, anagrelide, navelbine, fadrazole, tamoxifen, toremifene, testolactone, anastrozole, letrozole, vorozole, bicalutamide, lomustine, and carmustine.

10. The pharmaceutical composition of claim 9, wherein the anticancer drug is at least one selected from the group consisting of paclitaxel, interferon alpha-2a, carboplatin, doxorubicin, cisplatin, gemcitabine, 5-fluorouracil, cetuximab, leucovorin, irinotecan, oxaliplatin, capecitabine, docetaxel, and sorafenib.

11. The pharmaceutical composition of claim 8, wherein the cancer is resistant cancer, recurrent cancer or metastatic cancer.

12. The pharmaceutical composition of claim 11, wherein the cancer is resistant to at least one anticancer drug selected from the group consisting of cetuximab, panitumumab, irinotecan, vinorelbine, capecitabine, leucovorin, oxaliplatin, cisplatin, carboplatin, sorafenib, 5-fluorouracil (5-FU), bevacizumab, aflibercept and regorafenib.

13. The pharmaceutical composition of claim 8, wherein the cancer is any one or more cancers selected from the group consisting of colorectal cancer, breast cancer, uterine cancer, fallopian tube cancer, ovarian cancer, stomach cancer, brain cancer, rectal cancer, small intestine cancer, esophageal cancer, lymph gland cancer, gallbladder cancer, lung cancer, skin cancer, kidney cancer, bladder cancer, blood cancer, pancreatic cancer, prostate cancer, thyroid cancer, endocrine adenocarcinoma, oral cancer, and liver cancer.

* * * * *